Figure 1:
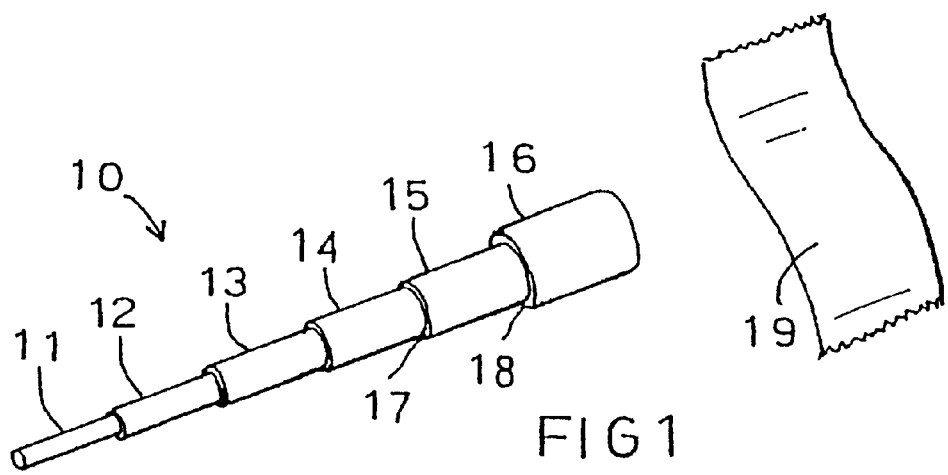

United States Patent [19]

Stenström

[11] Patent Number: 6,084,941
[45] Date of Patent: Jul. 4, 2000

[54] DEVICE FOR VISUAL MEASUREMENT OF DIMENSIONS

[75] Inventor: Hugo B. Stenström, Linköping, Sweden

[73] Assignee: Calluna Ide AB, Trosa, Sweden

[21] Appl. No.: 09/117,993

[22] PCT Filed: Feb. 14, 1997

[86] PCT No.: PCT/SE97/00238

§ 371 Date: Aug. 19, 1998

§ 102(e) Date: Aug. 19, 1998

[87] PCT Pub. No.: WO97/31570

PCT Pub. Date: Sep. 4, 1997

[30] Foreign Application Priority Data

Feb. 29, 1996 [SE] Sweden .................................. 9600779

[51] Int. Cl.⁷ ...................................................... H05G 1/28
[52] U.S. Cl. ........................... 378/162; 378/163; 378/165
[58] Field of Search .................... 378/162, 163, 378/165

[56] References Cited

U.S. PATENT DOCUMENTS 4,873,707 10/1989 Robertson .................................. 378/18
5,149,965 9/1992 Marks .

*Primary Examiner*—David P. Porta
*Assistant Examiner*—Pamela R. Hobden
*Attorney, Agent, or Firm*—Watson Cole Grindle Watson, P.L.L.C.

[57] ABSTRACT

A device for direct, visual estimation of dimensions of measurement objects that are difficult to reach, such as organs and foreign articles within human and animal bodies. The human eye gives a good size apprehension when comparing a measurement object with a similar thing of known dimension close to that of the measurement object. The comparison can be carried out on an X-ray picture in which a measurement object as well as a comparison body are reproduced close to each other and on the same scale. Means are provided for fixing the comparison body at the exterior surface of the human or animal body. The comparison body is confined by a series of surfaces of revolution with different sizes within an interval matched to the dimension interval of the dimension object. The form of the surfaces of revolution is matched to the form of the measurement objects, such as cylindrical surfaces of revolution being chosen if the measurement object is cylindrical and spherical surfaces of revolution being chosen if the measurement object is globular.

12 Claims, 3 Drawing Sheets

DEVICE FOR VISUAL MEASUREMENT OF DIMENSIONS

The present invention relates to a device comprising a body with known dimensions so designed that, through a simple, visual comparison between the body and a measurement object you can get a good appreciation of the body dimensions. (This should be valid irrespective of whether the object can be regarded directly or via a chain of information transformations, finally resulting in a picture of the object.) The invention has its primary application at the measurement of dimensions of objects that are difficult to reach, e.g. organs and foreign bodies within humans and animals.

The invention is founded on the fact that the human eye, badly equipped for absolute size estimation, gives strikingly good accuracy when comparing similar objects placed near each other. As an exception the comparative measurement may be accomplished at direct watching the measurement object, but as a rule a reproduction of the measurement object is watched. The picture is normally an X-ray picture but may, alternatively be produced with other electromagnetic radiation, such as infrared or visible light (in connection to endoscopic activity) or with ultrasonics. It can be directly analogue, as on a photographic film or digital and presented at a display.

A common way to measure the size of reproduced objects is to introduce a graded scale, e.g. a ruler. The dimensions of the object can then be measured at the picture and the measurement results transferred to the scale at the picture, where the real measure can be read. This implies, however, an active measurement with ruler or compasses or the like by means of which the measurement value can be transferred.

In modern X-ray installations the picture is digital and visible at a viewing screen. This is covered with a protecting glass. This glass prevents the compasses from reaching the very picture. If you try to measure you will get measurement errors or uncertainties because of parallax as well as due to perspective related scale distortion. Additionally, the scale normally is different for the reproduction in the digital picture of the object and the ruler. The reason is that the object and the ruler are not situated in the same plane. Modern zoom technology adds another scale factor. This does not facilitate the establishment of the correct product of all more or less known scale factors. Extensive additional work in the form of checking, retakings and recalculations is required. This takes long time, implies in itself a source of error and may further increase the X-ray exposure of the patient and the radiologist.

One has tried to avoid these disadvantages by replacing the ruler by a scale introduced in the very blood-vessel as part of a catheter, a so-called measurement catheter. Said part is provided with a row of marks of radioopaque material aligned in the longitudinal direction of the catheter. Like the measurement object they are visible at the X-ray picture. One example of embodiment of a measurement catheter is given in the patent letter DE 42 15 119 A1. Instead of distances between scale marks determined lengths of X-ray transparent material are here used as longitudinal length measure.

The french patent letter FR 8804892 presents another variant of measurement catheter the image of which, to the extent it can be measured, provides a possibility to create an opinion of the scale of the reproduction. The catheter image also provides a possibility to calculate to which extent the direction of the catheter in the human body deviates from being perpendicular to the X-rays. The deviation can be calculated from the geometry of the catheter image.

Measurement catheters are all intended to be introduced percutaneously in the human body. Their use therefore involves a risk of infection and wastes considerably the expensive time of the doctor and of his assistants. They are also very expensive.

Measurement catheters allow fairly the reading of the longitudinal size of observed organs to the extent that the measurement catheter can enter the domain the length of which is of interest. In practice, however, it has shown that they give poor accuracy when you try to measure transversally, e.g. the diameter of a blood-vessel or of part of it occluded by calcification. Good diameter measurement accuracy is a condition, however, for the proper choice of size of therapy aids. Examples of such aids are balloons for widening blood-vessels and so-called stents, which help to keep the blood-vessels-open.

As a consequence of the characteristics of such X-ray systems and measuring instruments as are used today a measurement tool that rapidly and without recalculation gives improved accuracy, hygiene and economy is demanded for since long. The demand has become accentuated after the change-over from photographic film to digital screen, where the very picture cannot be reached for measurements.

Through the invention a simple and handy tool for visual size measurement is provided in the form of a body which is small and easy to place at the exterior/surface of a human or animal body and which also can be used in connection with surgery in that it is hygienic and sterilizable.

The device according to the invention comprises a comparison body made of radioopaque material, said body being confined by a series of similar surfaces of revolution with between themselves different, known diameters within an interval. The form of the surfaces of revolution is matched to the form of the measurement objects and the diameter interval is matched to the dimension interval of the measurement objects. Means are arranged for fixing the comparison body to the exterior/surface of the human or animal body at a place near the measurement object.

In an embodiment preferred for measurement objects which are not cylindrical said surfaces of revolution are essentially spherical.

In an embodiment preferred for cylindrical measurement objects said surfaces of revolution are cylindrical and have mutually coinciding axis direction.

In this embodiment the lengths of the cylindrical surfaces of revolution are preferably clearly defined and dimensioned to form size reference in the axis direction.

At use in connection with X-ray interventional operations the comparison body is arranged for being sterile.

When the comparison body has cylindrical surfaces and is designed for measurement of diameters of anatomical tubular structures the diameter interval of the cylindrical surfaces of the body is matched to the interval within which said structures vary.

Then, by chosing the diameter series so as to correspond to common sizes of catheters for percutaneous transluminal angioplasty, the choice of catheter size, e.g. for balloon dilatation of blood vessels, is further facilitated.

For delivery in a guaranteed sterile state the comparison body is preferably arranged to be supplied within at least one tight package, which also can contain means of fastening and fixing the comparison body.

In one embodiment, preferred when the device is to be used twice, consecutively, its means of fixing its comparison body comprise two adhering surfaces, each with a protective foil that can be peeled off.

Figure 2:
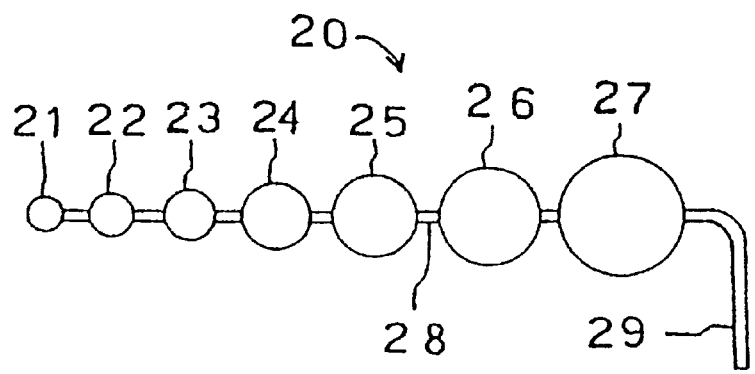
Figure 3:
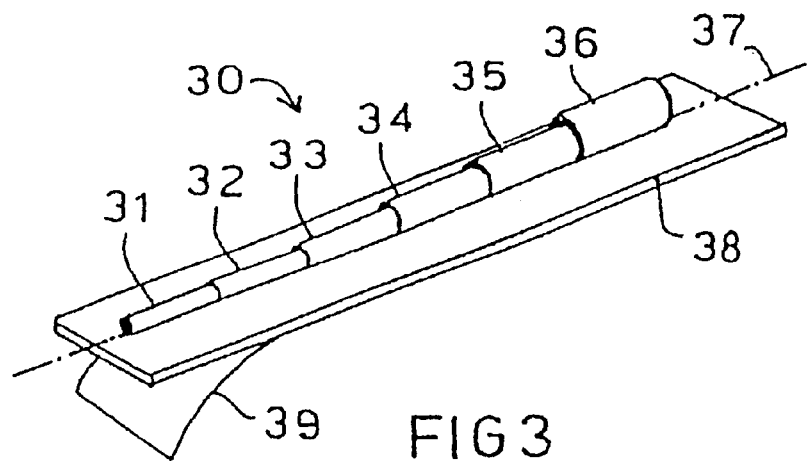
Figure 5:
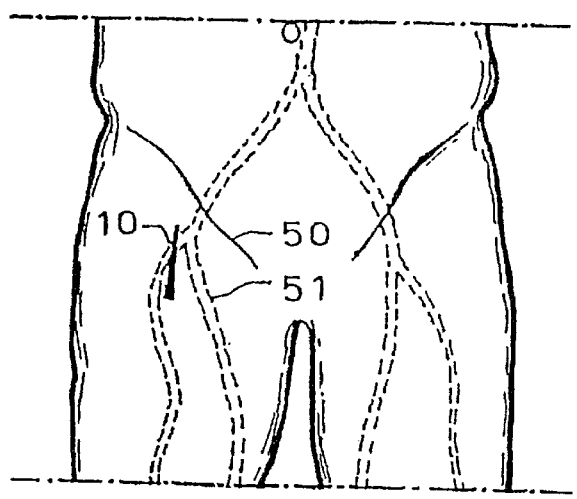
Figure 6:
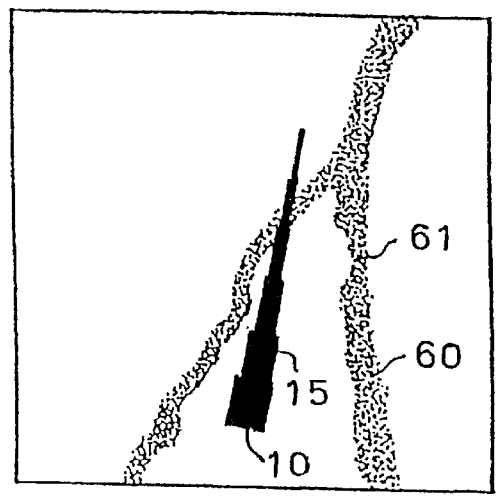
Figure 7:
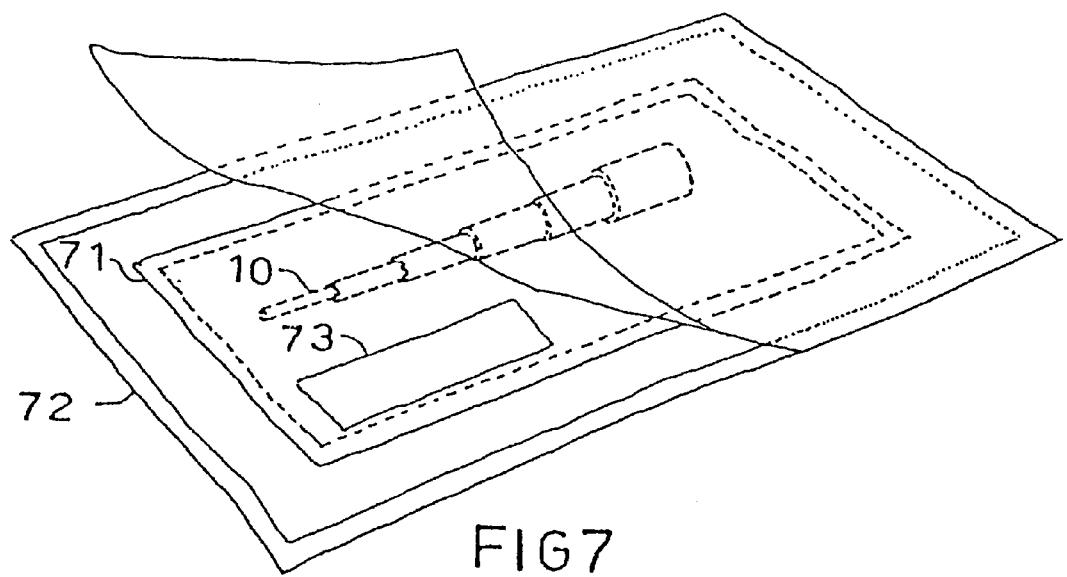
Figure 8:
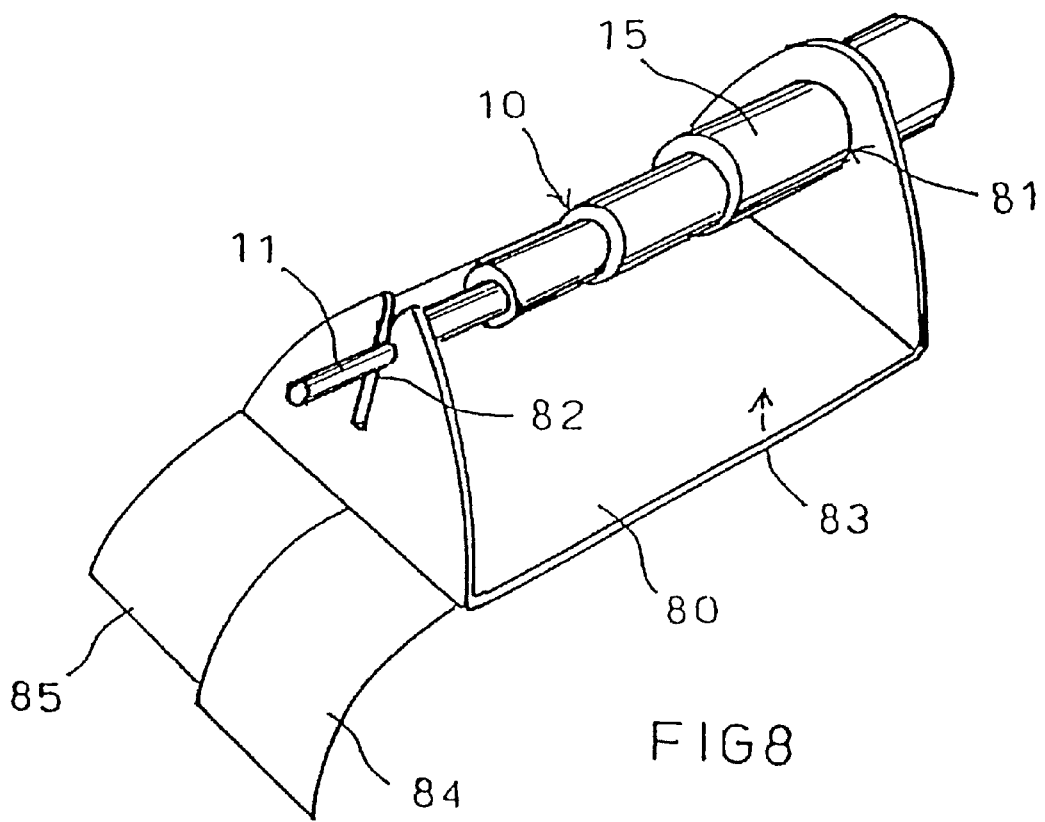

The invention and an example of its use are described in more detail with reference to the accompanying drawings, in which FIG. 1 shows a perspective view of an example of device according to the invention, where the rotation surfaces of the comparison body are cylindrical and the means for fixing this body is a simple tape, FIG. 2 in view from above shows an example of device according to the invention, where the rotation surfaces of the comparison body are spherical, FIG. 3 shows a perspective view of a device according to the invention, the comparison body of which has cylindrical surfaces with parallel axes and the means of fixing of which comprise a sticking plate, FIG. 4 in view from above shows an example of device according to the invention the comparison body of which has spherical rotation surfaces and is suitable for being cast in a form, FIG. 5 in view from above shows an example of placing of the comparison body in FIG. 1 near a groin at angiographic X-ray examination of a patient lying on his back, FIG. 6 shows a scetch after an X-ray picture received in the examination just mentioned at which dimensions of the comparison body and of blood vessels can be compared directly, FIG. 7 shows a device according to the invention the comparison body of which is packaged in an inner pack which, together with tape for its fixing, on its part is packaged in an outer pack and FIG. 8 shows a device according to the invention, where the means of fixing the comparison body are fitted to be used twice, consecutively.

The FIGS. 1 and 2 give examples of simple embodiments of the invention. In each figure the comparison body has the form of a simple rotational body, 10 and 20, respectively which is easy to manufacture, e.g. by turning. Its material should be metal, e.g. stainless steel. The body 10 as well as the body 20 has a form characterized by a series of surfaces of revolution. At the body 10 these are cylindrical, 11–16, at the body 20 they are spherical, 21–27. The surfaces of revolution in each series have different sizes within an interval matched to the dimension interval of the measurement objects.

If the measurement object is essentially cylindrical a comparison body 10, 30 (FIG. 3) with cylindrical surfaces of rotation 11–16, 31–36 is used. Because of the fact that the measurement object and the size reference have the same character their visual comparison will be accurate. The comparison body should be placed in such a way that the diameter of each cylindrical surface stands out distinctly. The comparison will be best if the common axis direction of the cylindrical surfaces of the comparison body is put parallelly to the axis of the cylindrical measurement object.

In the example in FIG. 1 the cylindrical surfaces of rotation are arranged according to diameter. The diameters of the cylindrical surfaces are in this example in order of size 2, 3, 4, 5, 6 and 8 mm, corresponding to common sizes of balloon catheters used in percutaneous transluminal angioplasty or similar procedures. Measurements with a comparison body of such design makes it possible to choose, rapidly and correctly, catheter for such procedures. This in its turn eliminates cases, when a catheter with unappropriate dimension would be used or tested with the accompanying risk of infection, injury and bleedings. Additionally, large, expensive time is saved for several persons as well as large cost for the catheter wrongly selected.

Sometimes the measurement object is not cylindrical but e.g. spherical, concentrated or irregular. An example of an object with concentrated form is a so-called aneurysm, that is a bag-like bulge at an artery, e.g. in the skull. At such measurement objects a comparison body 20, 40 (FIG. 4) limited by spherical surfaces of rotation 21–27, 41–47 is preferred. These surfaces are consecutively joined by fixing means. Such a joint can be an intermediate piece 28 with a radial extension much smaller than that of the spherical surfaces 26, 27 that are joined by that piece. Spherical surfaces of rotation 41–47 may also be joined by another structure 48 of such character that it very little encroaches the visibility of the contours of the spherical surfaces.

Comparison bodies 20, 40 with spheres have the advantage that the spheres offer measure reference in all directions. Their use has the condition that the comparison body is so placed and oriented that all its spheres are visible at the picture. In FIGS. 2 and 4 the spherical surfaces of the comparison body are arranged according to size. Their diameters form a series. The series may be geometric. So is e.g. the case in the comparison body 20, in which the quotient between adjacent diameters is $\sqrt[4]{\sqrt{2}} \approx 1.19$. The geometric series offers a.o. the advantage that the relative error at size comparison turns out to be essentially constant over the whole range of measurement.

FIGS. 1 and 2 also give different examples of simple means of fixing the comparison body. In FIG. 1 said means is simply a piece of tape 19. In FIG. 2 it is a bent protuberance 29 at the comparison body 20. This prevents the latter from rolling away from its place and orientation in the neighbourhood of the measurement object. Suitably designed such a protuberance also can facilitate further fixing with tape to the patient in a proper direction and in the neighbourhood of the measurement object.

The comparison body does not need such a shape that that can be manufactured by turning in one piece. If it is composed of cylindrical pieces, these, according to FIG. 3, e.g. can be arranged with a common base-line 37 to a continuous body, 30. This embodiment has the advantage that the body, along its base-line 37 can be fixed to one side of a flat base 38, the other side of which being prepared with a sticking agent protected by a detractable strip 39. Thus completed this comparison body 30 is simple to fix in desired position in the neighbourhood of the measurement object. It can be molded of a thermoplast with such a composition that it is impenetrable for the radiation used. Most often X-rays are used. Then the thermoplast has to be radio-opaque which implies addition of a dense substance, e.g. barium sulphate. The base 38, however, is made of material transparent for X-rays. Also other types of comparison bodies 10, 20, 40 can be made in a mold. This manufacturing method is specially suitable, when single use is justified, e.g. in hospitals in connection with surgical procedures and radiological interventions. In such environment a disposable type of comparison body can render profit assigned to rational and time-saving handling and increased safety.

FIG. 1 gives also an example of how a comparison body 10 with cylindrical surfaces can be given the function of a scale for measurements in the longitudinal direction of the measurement object. The ring-formed surfaces 17,18 between adjacent cylinder surfaces 14, 15 and 15, 16 respectively, as well as the ends of the comparison body, are perpendicular to the direction of the axis of the cylinder surfaces. Thus they mark distinctly the ends of the cylinder surfaces and make with this the length of each cylinder surface well defined. In this very example each one of the cylinder surfaces has been given one and the same length, 10 mm.

Figure 4:
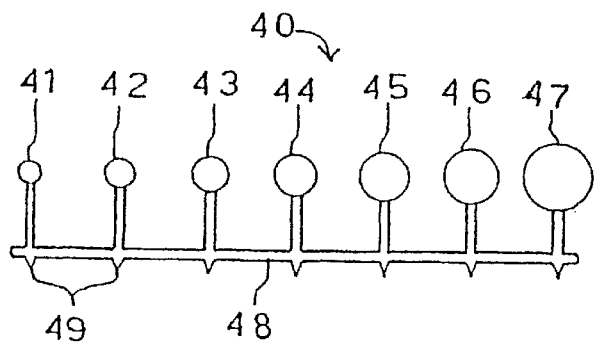

In FIG. 4 you can likeways see an example of how a comparison body 40 with spherical surfaces also may contain a scale for longitudinal and distance measurement. In this case said scale is realized as a number of protuberances 49 from the structure 48. To become distinct at an X-ray picture these should end with an edge orthogonal to the plane of the figure—not with a point. The structure 48 is made in a mold and is of X-ray dense material.

The use of the comparison body is further illuminated in the FIGS. 5 and 6. FIG. 5 describes how a comparison body 10 according to the invention is applied to a patient near his groin in order to be close to the area with blood vessels 51 which will be examined with X-rays. FIG. 6 is a drawing after an X-ray picture of said area, showing the close to obvious way in which the size of the vessels is visually read: The vessel diameter at 60 is as large as the next largest cylinder surface 15 of the comparison body 10, that is 6 mm, whilst the narrow part at 61 is somewhat longer than the length 10 mm of a cylinder surface of this comparison body.

In applications where you cannot place the comparison body and the measurement object at about the same distance from the radiation source or (as an exception) from the eye at direct observation, you have to correct the measurement result by a distance factor which is the quotient between the distance of the comparison body from the radiation source and that of the measurement object. In order to avoid calculation work it is then practical to use a comparison body in which the diameters of the surfaces of revolution are dimensioned to form a geometric series with a certain quotient. The body 20 with spherical surfaces of rotation as well as the body 30 with cylindrical surfaces of revolution were drawn according to this principle. When placing such a comparison body you should see to it that said distance factor will be just said quotient (or, if necessary, a power thereof). Instead of recalculating the measurement result you then read the diameter of the measurement object as the diameter of the next smaller surface of rotation referred to the one which corresponds to the diameter of the measurement object at the picture. This is valid if the radiation source (as usually is the case) is below (behind) the measurement object. Is the radiation source above (in front of) the measurement object you read instead the next larger surface of rotation.

Means 19, 29, 38, 39, 48 of fixing the comparison body in the neighbourhood of the measurement object were described above. Another means, which can replace or complete those is shown in FIG. 7. It comprises a package 71 containing the comparison body 10. The package 71 is preferably a plastic bag, in common way sealed under vacuum. This bag with its contents is easy to fasten with tape at desired spot in the neighbourhood of the measurement object.

When sterility is demanded said package 71 with its contents should be enclosed in an outer package 72. A strip of tape 73 or similar is bypacked. The package 72 is preferably a plastic bag, too. It is also sealed. The whole content of the outer bag is arranged to be sterile. Most simple is to deliver this bag with its contents sterilized by common means. At use the outer package is opened and the sterile inner package 71 with its comparison body 10 is fastened at the desired spot with the by-packed and likewise sterile strip of tape 73. Also other types of comparison bodies, e.g. 20 and 40 can of course be delivered packaged and sterilized as above.

Sometimes, at one and the same examination occasion there is a need to use the device according to the invention in more than one area at the patient without neglecting the sterility demand. A simple example of embodiment allowing that is shown in FIG. 8. The comparison body 10 of the device is here mounted in a yoke 80. Its thick end is locked in a circular notch 81 in the yoke by means of the "chest of drawers" effect. Its fine end 11 is introduced in a resilient snap lock 82. The lower surface 83 of the yoke is made sticky, e.g. with the aid of cement or double-adhesive tape. The sticky surface is covered with a protection foil divided into two detractable strips 84, 85.

The yoke design has the advantage that the comparison body 10 serves as a good handle, when the device is to be set free from a protection strip 84 and be fastened at the patient in a proper area and in a proper direction. Then the untouched protection strip 85 will allow uncovering a new, fresh, sticking surface so that the device can be fastened for use in a new position.

Within the scope of the invention you will find not only those examples which have been illustrated with figures. For instance a comparison body with cylindrical surfaces has not to consist merely of massive cylinders but can as well comprise pieces of tubes or rings of such a meterial and with such a wall thickness that they are X-ray dense. Thin rings can e.g. be made of gold.

For special applications, in a device with comparison body according to the invention, this body can be combined with another, X-ray dense comparison body. The latter is then fastened at the former. It can but has not to be designed with a series of surfaces of rotation as according to the invention. For example a device according to FIG. 2 can be combined with a thin ring. This can be fastened e.g. to the protuberance 29.

As other X-ray equipment is perfected the difficulty increases to carry through accurate size measurements, e.g. in order to choose the right size of balloons for widening of blood vessels. The photographic film is more and more replaced by digitally produced pictures, primarily visible at a TV-monitor. In the chain up to the visible picture you may find picture amplifiers of different size and with "zoom" capability, that is magnification of optional part of the picture at the viewing screen. Turning the tube and the picture amplifier is substituted for turning the patient. This results in a considerable variation in the degree of magnification. The disadvantage of that is eliminated with the aid of the invention in that said variation will be essentially the same for the measurement object and the comparison body.

The need of measuring with a ruler and of re-calculating the size in the picture at the TV-monitor is eliminated. The procedure, last mentioned, which till now has been needed irrespective of whether the size reference is a ruler under the patient or a measurement catheter in the actual blood vessel, gives relatively large errors. The errors arise a.o. because you cannot place the ruler close to the picture because of the protection glass that is fitted in front of the viewing screen of the monitor. Additionally, said procedure is relatively time-consuming. Use of the invention saves time to skilled laboratory personnel and gives without waste of time and with good reliability the attending doctor the information he needs.

Further the invention can make it possible to make measurements that cannot be made in other way. Aneurysm (varices in the brain) are e.g. often too small to be seen with computer tomography.

The comparison body does not need to be applied directly to the skin of the patient. Often the person that will be X-ray examined is covered with a cloth. In such cases it is convenient to apply the comparison body to that cloth.

What is claimed is:

1. A device for direct visual reading at X-ray examination of dimensions of measurement objects, difficult to get at, in bodies of people and animals, which device contains a comparison body (10,20) made of X-ray dense material, wherein said comparison body (10,20) is confined by at least four similar surfaces of revolution (11–16, 21–27) each surface of revolution having a diameter, each said diameter being different and known, said surfaces of revolution (11–16, 21–27) forming a series with a quotient between consecutive diameters within an interval of $\sqrt[4]{\sqrt{2}}=1.19$ to 1.5, and wherein said comparison body shows fittings for being placed, directly or indirectly, at the exterior surface of the human or animal body so close to the measurement object and so oriented that one and the same X-ray exposure will give an image not only of the measurement object but also, close to it, of the comparison body.

2. The device as claimed in claim 1, wherein the fittings are constituted by aids, such as a protuberance (29), a plate (38), a structure (48) and a yoke (80) for proper placing and orienting the comparison body before the exposure.

3. The device as claimed in claim 1, wherein said surfaces of revolution (21–27, 41–47) are spherical and are joined by a structure (28, 48) in the shape of pieces with a radial extension smaller than that of the spherical surfaces (21–27, 41–47) that very little encroaches the visibility of the contours of the spherical surfaces.

4. The device as claimed in claim 2, wherein said structure (48) being made of X-ray dense material in a mould.

5. The device as claimed in claim 2, wherein said structure (48) comprises a scale (49) made of X-ray dense material.

6. The device as claimed in claim 1, wherein said surfaces of revolution (11–16) are cylindrical and have mutually coinciding axis direction, the lengths of the cylindrical surfaces of revolution being defined and dimensioned to form size reference in the axis direction to form a scale.

7. The device as claimed in claim 6, wherein the diameters of the series of cylindrical surfaces (11–16) correspond to current sizes catheters used for percutaneous transluminal angioplasty procedures.

8. The device as claimed in claim 1, wherein means (19, 38, 71, 80) showing sticking surfaces are arranged for fixing the comparison body directly or indirectly to the exterior surface of the human or animal body at a place near the measurement object.

9. The device as claimed in claim 8, wherein the means (80) for fixing the comparison body to the exterior of the human or animal body comprise at least two adhering surfaces (83), each with a protective foil (84, 85) that can be peeled off.

10. A method at X-ray examination of dimensions of objects that are difficult to reach human and animal bodies by means of a device comprising a comparison body (10, 20) made of X-ray dense material, said comparison body being confined by a series of similar surfaces of revolution (11–16, 21–27) with between themselves different, known diameters within an interval, wherein said surfaces of revolution (41–47) are chosen spherical for application on aneurysms, before exposing the measure object together with the comparison body to X-rays, the comparison body being placed directly or indirectly, at the exterior surface of the human or animal body so close to the measurement object and so oriented that one and the same X-ray exposure will give an image not only of the measurement object but also, close to it, of the comparison body, the measurement object and the comparison body being exposed to X-rays, and at their common picture, directly and visually the measure of the comparison body best coinciding with the wanted dimension of the measurement object is read.

11. A method at X-ray examination of dimensions of objects that are difficult to reach human and animal bodies by means of a device comprising a comparison body (10, 20) made of X-ray dense material, said comparison body being confined by a series of similar surfaces of revolution (11–16, 21–27) with between themselves different, known diameters within an interval, wherein the surfaces of revolution (11–16) are chosen cylindrical for application on anatomical objects which are not aneurysms, in particular tubular structures before exposing the measure object together with the comparison body to X-rays, the comparison body being placed directly or indirectly, at the exterior surface of the human or animal body so close to the measurement object and so oriented that one and the same X-ray exposure will give an image not only of the measurement object but also, close to it, of the comparison body, the measurement object and the comparison body being exposed to X-rays, and at their common picture, directly and visually the measure of the comparison body best coinciding with the wanted dimension of the measurement object and said surfaces of revolution (41–47) are chosen spherical for application on aneurysms.

12. The method as claimed in claim 11, wherein said cylindrical surfaces (11–16) have mutually coinciding axis direction and in that the comparison body is oriented with their common axis direction approximately in parallel to said structure.

* * * * *